United States Patent [19]

Robertson

[11] Patent Number: 4,619,672

[45] Date of Patent: Oct. 28, 1986

[54] FILTER FOR LASER SURGERY SMOKE EVACUATION SYSTEM

[75] Inventor: Philip D. Robertson, Colorado Springs, Colo.

[73] Assignee: Xanar, Inc., Colorado Springs, Colo.

[21] Appl. No.: 774,694

[22] Filed: Sep. 11, 1985

[51] Int. Cl.⁴ .............................................. B01D 50/00
[52] U.S. Cl. ........................................ 55/316; 55/318; 55/485; 55/502; 55/505
[58] Field of Search ................. 55/316, 318, 485, 501, 55/502, 505, 482

[56] References Cited

U.S. PATENT DOCUMENTS

| | | | |
|---|---|---|---|
| 2,728,407 | 12/1955 | Squier | 55/502 X |
| 2,976,143 | 6/1957 | Longenecker et al. | 55/316 |
| 2,988,169 | 6/1961 | Klein | 55/502 |
| 3,406,501 | 10/1968 | Watkins | 55/316 |
| 3,513,643 | 5/1970 | Tarala | 55/485 X |
| 3,568,416 | 3/1971 | Staunton | 55/316 X |
| 3,906,798 | 9/1975 | Dray | 55/318 X |
| 4,141,703 | 2/1979 | Mulchi | 55/316 |
| 4,396,206 | 8/1983 | Tsuge et al. | 55/316 X |
| 4,444,575 | 4/1984 | Miller et al. | 545/485 X |
| 4,487,606 | 12/1984 | Leviton et al. | 55/482 X |

Primary Examiner—Kathleen J. Prunner
Attorney, Agent, or Firm—Donal B. Tobin

[57] ABSTRACT

A filter for a laser surgery smoke evacuation system including a generally cylindrical hollow housing with endcaps on either end to hold a plurality of filter elements in place within the housing. The inlet end of the housing includes a hollow cone with a cylindrical inlet projecting from the apex of the cone and a base ring projecting from the base of the cone. The endcaps are held in place by adhesive tape strips with a high friction backing. The high friction backing helps hold the filter lightly in place during use. The filter is disposable and easily removable from the system and includes no mechanical apparatus to hold the filter in the system.

4 Claims, 4 Drawing Figures

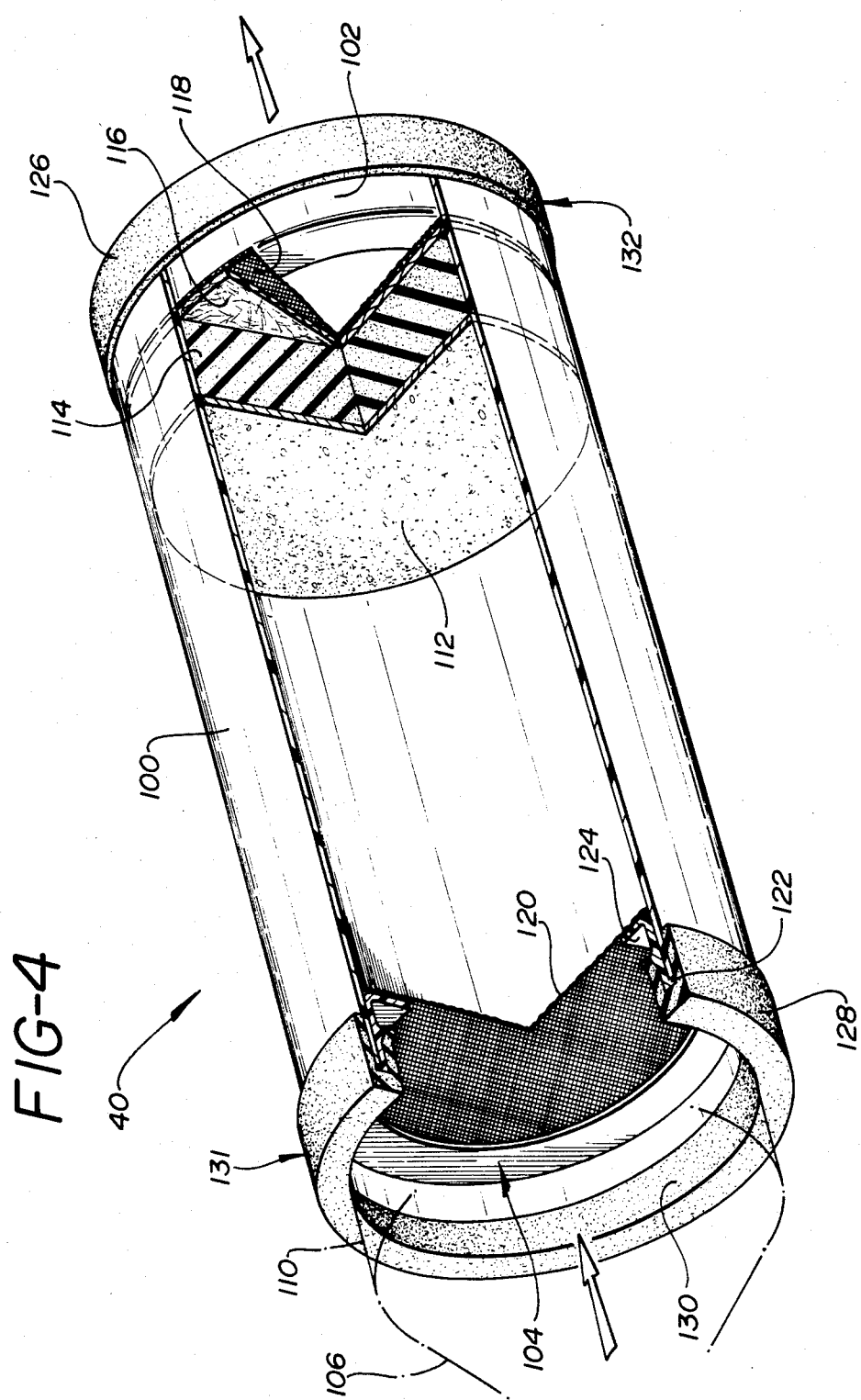

FILTER FOR LASER SURGERY SMOKE EVACUATION SYSTEM

THE FIELD OF THE INVENTION

This invention relates to an apparatus for evacuating the undesired by-products of laser surgery from the surgical site by establishing an airflow through a suction tube placed at the surgical site and more particularly to a filter used with the apparatus.

BACKGROUND OF THE INVENTION

Related Applications

The present application relates to a filter for a laser surgery smoke evacuation system. Two other applications are being filed simultaneously and are assigned to the same assignee as the present application: the first, U.S. Application Ser. No. 774,692, relates to the smoke evacuation system as a whole; and, the second, U.S. Application Ser. No. 774,693, relates to electronic circuitry for the system.

Laser surgery is becoming a more common surgical modality with a large variety of uses. When a tissue is subjected to a high energy laser beam the tissue is vaporized. It is desirable to remove the vapor and other by-products from the surgical site in a controlled manner. Smoke is intended to mean the by-products of laser surgery which are primarily gases, but can include some small amounts of liquid and solid particulate matter. The most common means of removing the vapor and other by-products is to use a suction tube at the surgical site to establish a flow of air which is then delivered to a filter placed in a housing with the motors and pumps that establish the vacuum flow. Present day vacuum apparatus usually works satisfactorily but are often heavy, difficult to move, noisy and expensive. The filters used with many present day systems can be difficult to replace when they become clogged.

It would be desirable to have an easily replaceable and disposable filter for laser surgery smoke evacuation system.

SUMMARY OF THE INVENTION

The present invention provides a light-weight disposable filter which may easily be replaced. The filter includes a generally hollow cylindrical housing with an inlet and an outlet. Endcaps are placed on each end of the housing. Each endcap is a generally annular ring having a flange extending radially outward from the exterior edge of the ring and having another flange extending radially inward from the interior edge of the ring. The flanges are preferably spaced axially along the ring. The outside diameter of the ring is slightly less than the inside diameter of the housing so that each endcap will fit snugly into the housing. A plurality of filter elements are disposed inside the housing and held in place by at least one of the endcaps. Inlet and outlet screens are held in place respectively by the endcaps. Adhesive tape strips extends circumferentially about the inlet and outlet ends of the housing and the tape strips wrap around the end of the endcaps and cover the outer circumferential surface of the outwardly extending flange and the interior surface of the ring portion of each endcap to hold the inlet and outlet endcaps in place on the housing. A high friction backing is placed on the adhesive tape strips and extends at least partially around the circumference of each tape. The high friction surface on the tape strips helps hold the filter in place during use.

Neither the filter nor the apparatus which holds it contains any mechanical locks or the like for holding the filter in place. The filter is held in place by the frictional engagement between the tape and the receptacle in which the filter is placed and by the vacuum provided by the system when it is in operation.

The filter also includes a hollow cone extending from its inlet end with a cylindrical inlet projecting from the apex of the cone and a base ring projecting from the base of the cone. The outside diameter of the base ring is slightly smaller than the inside diameter of the inlet cap and the filter housing. An adhesive bonding agent is applied to the exterior surface of the base ring and the confronting surface of the adjacent tape strips to provide adhesive bonding for the cone to the remainder of the filter.

A plurality of filter elements are placed inside the filter housing and include granulated charcoal mesh, disk shaped from filter elements downstream of the charcoal mesh, a plurality of fiberglass insulator elements downstream of the foam filter, and a plastic screen downstream of the fiberglass elements.

These and other features and advantages of the present invention will become apparent from the following detailed description of the preferred embodiments taken in conjunction with the following drawings:

DESCRIPTION OF THE DRAWINGS

FIG. 4 shows an assembled view of the filter shown in FIG. 3.

DETAILED DESCRIPTION OF THE PREFERRED EMBODIMENTS

Figure 1:
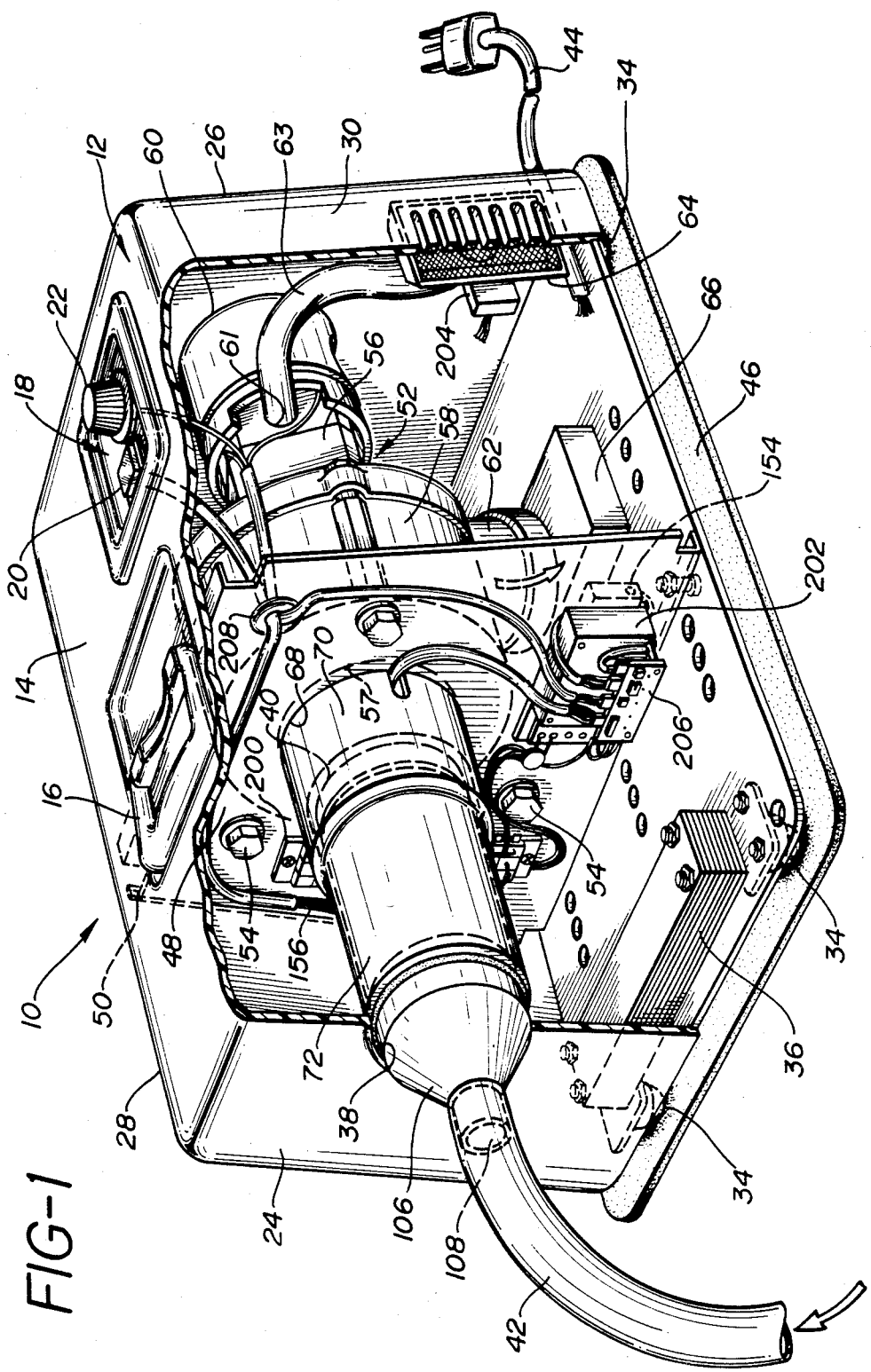
FIG. 1 shows a perspective view partly in section of the evacuator system of the present invention.

Referring the now to FIG. 1 there is shown a perspective view partly in section of the apparatus of the present invention. The evacuator system 10 of the present invention is housed in a casing 12 having a top surface 14 on which a handle 16 and a control panel 18 are mounted. Control panel 18 has a warning light to 20 to indicate a clogged filter condition and a control knob 22 for controlling the amount of suction provided by the apparatus. Casing 12 also includes a front surface 24, back surface 26 and sides 28 and 30. In the preferred embodiment, top 14, front 24, back 26 and sides 28 and 30 are all integraly formed of a high strength lightweight plastic material. A separate bottom panel 32 is removably affixed to casing 12 to provide an enclosure within casing 12. Wheels 34 are supported on bottom panel 32 for portability and counter weights 36 are used to balance the interior components.

Front surface 24 has a circular opening 38 therein through which filter 40 may be inserted into case 12. A suction tube 42 connects to filter 40 and has a convenient length for extending to the surgical site. An electrical power cord 44 provides power to the internal components of the system.

Still referring to FIG. 1 there are shown certain interior components of the system. A mounting plate 48 fits in grooves 50 on the interior of top 14 and sides 28 and 30. A centrifugal vacuum pump 52 is mounted by means of bolts 54 to mounting plate 48.

Vacuum pump 52 includes an alternating current multi-phase motor 56, an impeller chamber 58, an exhaust horn 62, an exhaust pipe 56 and optional exhaust muffler 66 mounted on bottom panel 32 to reduce exhaust noise. Impeller blades (not shown) are mounted on the shaft (not shown) of motor 56 and rotate within impeller chamber 58 to create a negative pressure in chamber 58.

The inlet 57 to impeller chamber 58 is a generally circular opening aligned coaxially with a circular opening 68 in mounting plate 48. Exhaust horn 62 from impeller chamber 58 extends tangentially from generally cylindrical impeller chamber 58 so that the airflow exits impeller chamber 58 without infringing upon the electrical windings of motor 56. As an alternative feature an exhaust pipe (not shown) may be connected to exhaust horn 62 and exit through an appropriate opening in casing 12 to connect with the normal exhaust in the operating room.

Figure 2:
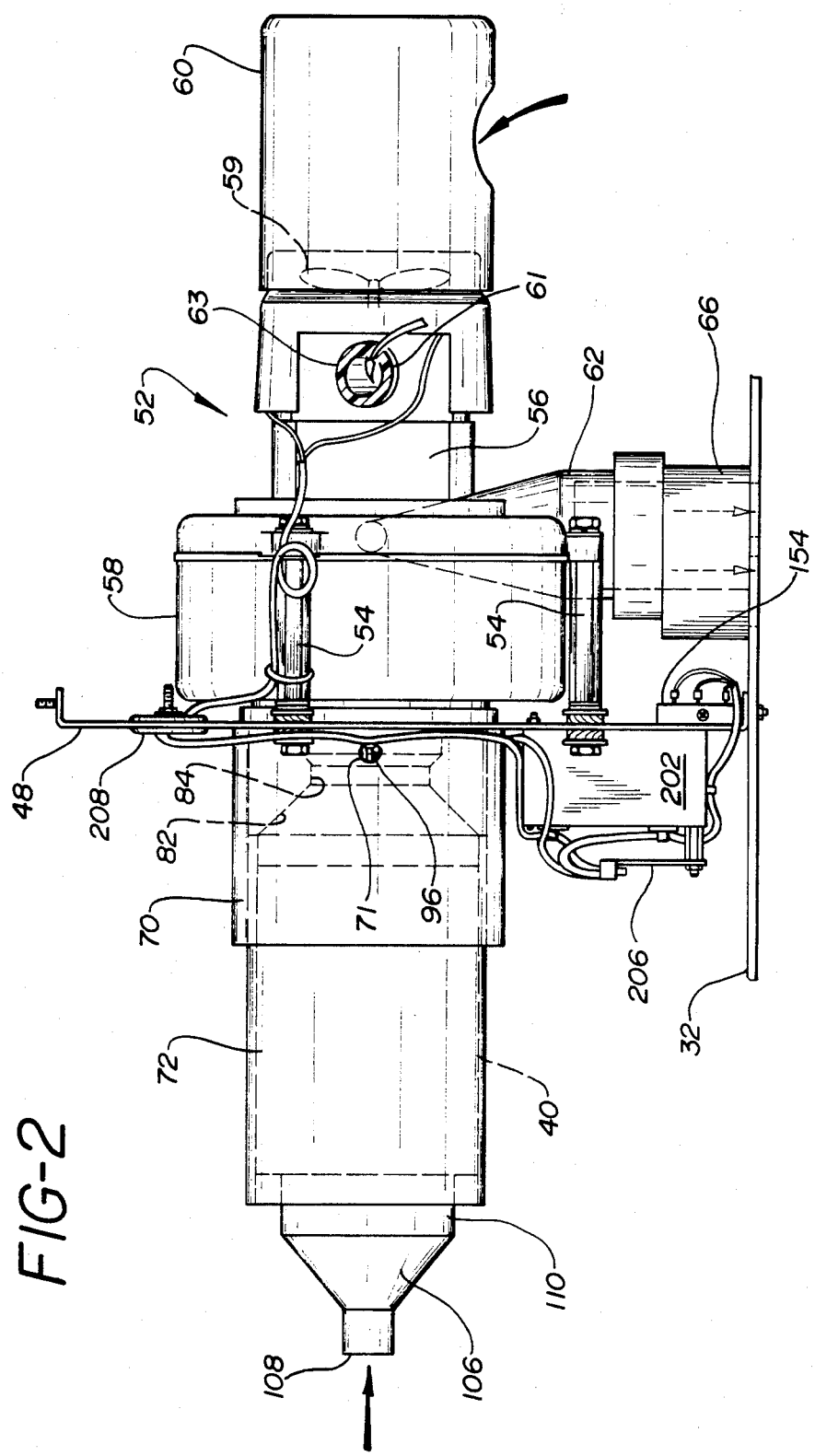
FIG. 2 shows a side elevation of key components of the apparatus of FIG. 1.

Referring now to FIG. 2 there is shown a filter collar 70 and filter duct 72, which are disposed on the opposite side of mounting plate 48 from vacuum pump 52 and aligned generally coaxially with vacuum pump 52. Filter duct 72 fits flush with opening 38 in the front wall 24 of casing 12 and receives filter 30. It is preferred that filter duct 72 are bonded to the peripheral surface of opening 38 to reduce vibration.

Filter collar 70 has access slot 71 through which a temperature sensing element 96 may be introduced to sense the clogged condition of the filter as is explained in copending applications mentioned in the Related Application section of this application.

Figure 3:
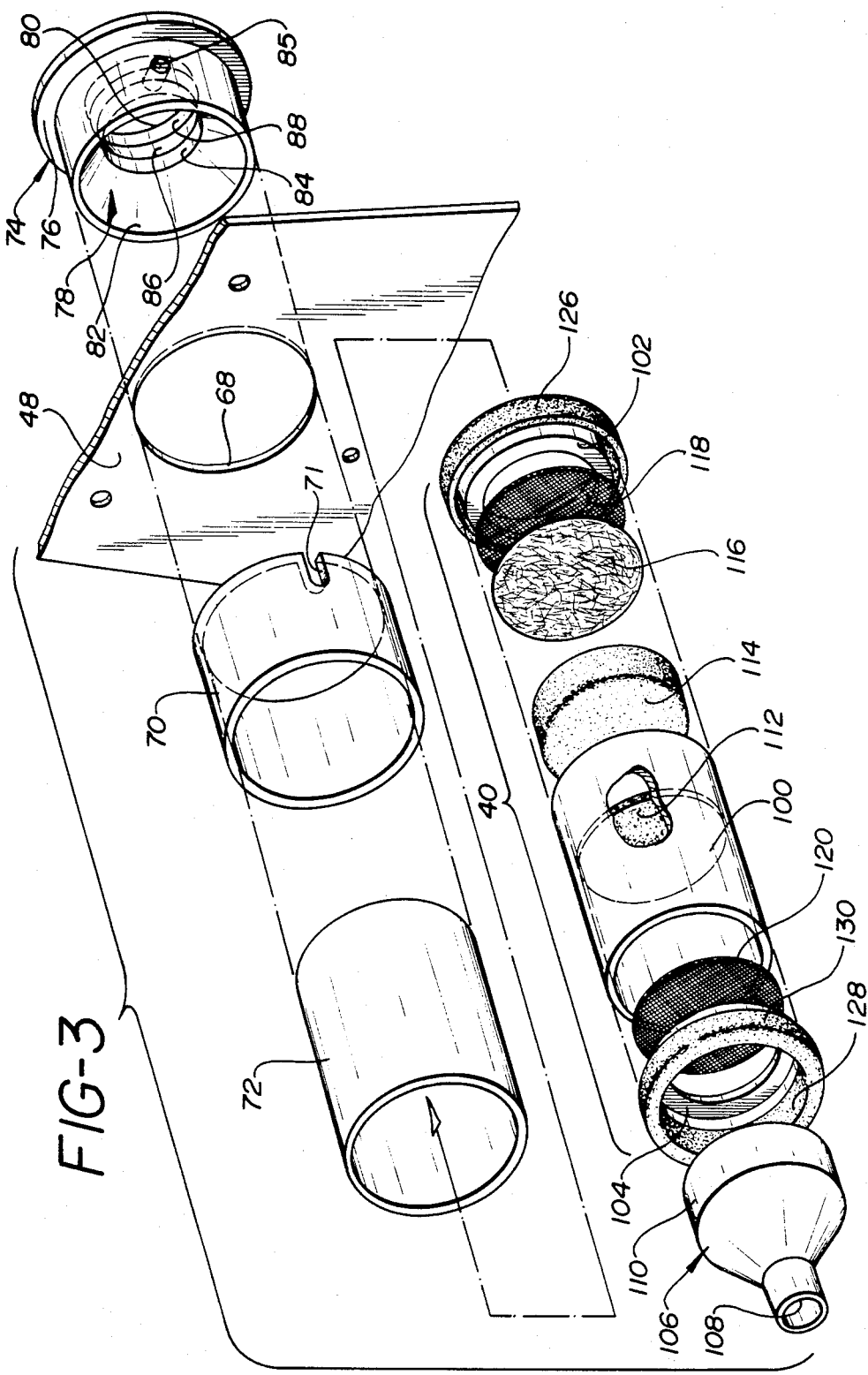
FIG. 3 shows an exploded perspective view of the filter used with the present apparatus.

Referring now to FIGS. 3 and 4 the construction of filter 40 will be discussed. Filter 40 includes a generally cylindrical housing 100 having endcaps 102 and 104. The inlet end of filter 40 is a cone 106 with a small cylindrical inlet 108 extending from the apex of cone 106 and a large cylindrical base 110 extending from the base of cone 106. Filter 40 is a hollow structure inside of which various filter elements are mounted including a granulated charcoal mesh 112 secured inside housing 100, a disk shaped foam filter 114 downstream of the charcoal filter, a disk shaped fiberglass insulator filter 116 downstream of foam filter 114 and a plastic mesh screen 118 preferably made of fiberglass downstream of the fiberglass filter 116. A similar screen 120 covers the inlet end of housing 100. Six staples (not shown) spaced evenly around housing 100 are used to hold endcap 102 and mesh screen 118 securely in housing 100. Endcap 102 is a generally cylindrical ring having a flange 122 extending radially outwardly on the outlet end of endcap 102 and an inwardly extending flange 124 on the interior portion of endcap 102. As shown particularly in FIG. 4 endcap 102 fits snugly inside the oulet end of housing 100 with flange 122 bottoming on the peripheral edge of the outlet end of housing 100 and flange 124 bottoming on screen 118 to hold the various filter elements in place within housing 100. A foam backed adhesive tape strip 126 is adhesively attached around the outside periphery of the outlet end of housing 100 and contacts the adjacent surface of flange 122 and then wraps around the end of flange 122 to adhesively bond to the inwardly facing surface of endcap 102.

Endcap 104 is similarly attached to the inlet end of housing 100 by means of a similar strip of tape 128 similarly wrapped around endcap 104 to hold screen 120 in place. Glue is applied to the internally facing surface 130 of tape 128 and to the exterior surface of base portion 110 of cone 106. The outside diameter of base 110 is such that base 110 conveniently slides into the inlet end of housing 100 and is glued to a portion of the inwardly facing surface 130 of tape 128. Cone 106 slides into the inlet end of housing 100 until base 110 bottoms on flange 124 of end cap 104. The outwardly facing surface 131 of tape 128 is exposed on the outside surface of housing 100. Similarly the outwardly facing surface 132 of tape 126 is also exposed on the outside surface of housing 100.

The diameter of filter duct 72 is such that filter 40 slides conveniently within filter duct 72 and the outwardly exposed surfaces 131 and 132 of tapes 128 and 126 provide light friction contact with the confronting interior surface of filter duct 72.

Filter 40 is held in place only by the vacuum provided within the system and has no locks or mechanical retainers. Thus filter 40 may be easily removed from filter duct 72 when it becomes clogged by merely turning off the vacuum pump 52. Suction tubes 42 extends from inlet 108 of cone 106 to the operative site. It will be appreciated that filter 40 is conveniently removable and completely disposable.

The operation of the filter will now be described. A clean filter 40 is placed in filter duct 72 and the system is energized so that motor 56 will turn on and start the impellers rotating inside impeller chamber 58 to develop a vacuum inside impeller chamber 58. Air enters the system through filter cone 106 through duct 72 past temperature sensor 96 into inlet 57 to impeller chamber 58 circulates through impeller chamber 58 with the aid of impellers (not shown) and exits through exhaust horn 62 either into the interior of casing 12 or optionally through exhaust pipe 65 and muffler 66 and exhaust openings in case 12 to the atmosphere.

When filter 40 becomes clogged the airflow through the fitting 74 decreases and the temperature rises. This increase in temperature is sensed by temperature sensor 96 which operates suitable described electronic circuitry to provide an alarm signal either by way of light 20 or an audible alarm. The system will operate with a clogged filter for approximately thirty minutes before a thermostat (not shown) turns the power to motor 56 off and shuts down the system. It is anticipated that a user will note the alarm signal and change the filter 40 long before the thermostat turns the system off.

Filter 40 is held firmly in place by the vacuum when the system is on. When the system is in operation tugging and pulling on suction tube 42 will not remove or loosen filter 40 from its position in filter duct 72 and will not affect the operation of the system. When one wishes to change the filter one merely turns off the power to dissipate the vacuum and then filter 40 is easily removable from filter duct 72 within a matter of a few seconds. The system may then be turned on again and the system is ready to operate again.

Referring again to FIG. 2 it is noted that there is a converging section 82 at the inlet of fitting 74. This converging section increases the airflow through filter 40 so that the laser surgery by-products which are principally gaseous are trapped in the filter. If the airflow is too slow not all of these by-products will be trapped by the filter and the byproduct gases may begin to desseminate into the air around the operative site.

It can be seen that the present invention provides a disposable filter for a laser surgery smoke evacuation system.

The present invention has been described in conjunction with certain preferred embodiments. Those skilled in the art will appreciate that many modifications and changes may be made to the preferred embodiments without departing from the spirit of the present invention. It is therefor, not intended to limit the present invention except to set forth in the following claims.

I claim:

1. A filter element for a laser surgery smoke evacuator system comprising:
    a generally cylindrical hollow housing having an inlet end and an outlet end;
    endcaps disposed about said inlet end and said outlet end and including a generally annular ring having a flange extending radially outwardly from an exterior edge of said ring and having a flange extending radially inwardly from an interior edge of said ring;
    the outside diameter of said ring being slightly less than the inside diameter of said housing to provide a snug fit therein for both said endcaps;
    a plurality of filter elements disposed within said housing and held in place by at least one of said endcaps;
    inlet and outlet screens held in place respectively by said endcaps;
    adhesive tape strips extending circumferentially about the inlet and outlet ends of said housing with said tape strips wrapping around said endcaps and covering the outer circumferential surface of said outwardly extending flange and the interior surface of the annular ring of each endcap and holding said inlet and outlet endcaps in place on said housing;
    a high friction backing on said adhesive tape strips extending at least partially around the circumference of said strips; and
    said high friction backing of said tape strips adapted to lightly hold said filter in place during use.

2. The filter of claim 1 further including:
    a hollow cone having an apex and a base;
    a cylindrical inlet projecting from the apex end of said cone;
    a base ring projecting from the base from said cone;
    the inside diameter of said base ring being slightly smaller than the outside diameter of the inlet endcap and said filter housing; and
    an adhesive bonding agent applied to the exterior surface of said base ring and to an interior surface of said tape strip on said inlet endcap to provide an adhesive bond there between.

3. The filter of claim 1 wherein said filter elements include:
    a granulated charcoal mesh disposed a short distance inside the outlet end of said housing;
    a disk shaped foam filter downstream of said charcoal mesh;
    a fiberglass insulator element downstream of said foam filter; and wherein said outlet screen is
    a plastic screen downstream of said fiberglass element.

4. The filter of claim 1 wherein said outwardly extending flange and said inwardly extending flange are spaced axially apart along said ring.

* * * * *